United States Patent [19]

Evans

[11] 4,148,820
[45] Apr. 10, 1979

[54] NOVEL PHENOL STABILIZERS

[75] Inventor: Samuel Evans, Basel, Switzerland

[73] Assignee: Ciba-Geigy Corporation, Ardsley, N.Y.

[21] Appl. No.: 786,177

[22] Filed: Apr. 11, 1977

[30] Foreign Application Priority Data

Apr. 14, 1976 [CH] Switzerland .................... 4750/76

[51] Int. Cl.² ........................................... C07C 69/96
[52] U.S. Cl. ........................... 260/463; 260/45.7 S; 528/175
[58] Field of Search ............... 260/463, 47 XA, 45.7 S

[56] References Cited

U.S. PATENT DOCUMENTS

| | | | |
|---|---|---|---|
| 3,506,716 | 4/1970 | Peterli et al. | 260/619 A |
| 3,510,507 | 5/1970 | Brown et al. | 260/463 |
| 3,579,561 | 5/1971 | Meltsner | 260/463 |
| 3,655,718 | 4/1972 | Schutze et al. | 260/463 |
| 3,737,486 | 6/1973 | Schutze et al. | 260/463 |
| 4,032,510 | 6/1977 | Floyd et al. | 260/463 |

FOREIGN PATENT DOCUMENTS 2016296 10/1971 Fed. Rep. of Germany.

Primary Examiner—Elbert L. Roberts
Assistant Examiner—Molly C. Eakin
Attorney, Agent, or Firm—Wenderoth, Lind & Ponack

[57] ABSTRACT

Phenols of the formula I

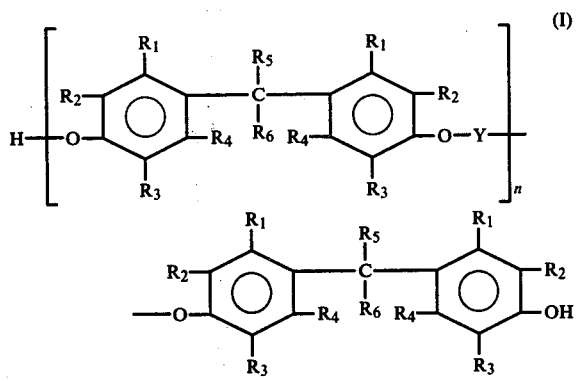

wherein
n has a value from 1 to 15,
each of $R_1$, $R_2$, $R_3$ and $R_4$ independently is a hydrogen atom, a $C_1$-$C_{18}$-alkyl group, an aryl group, a $C_5$-$C_{12}$-cyclo-alkyl group or a $C_7$-$C_{13}$-aralkyl group,
$R_5$ is a hydrogen atom or a $C_1$-$C_{18}$-alkyl group,
Y is a carbonyl, thiocarbonyl, sulphinyl, sulphonyl, $-P(OR_7)-P(=O)(OR_7)-$, $-P(=O)(R_7)-$ or $-P(R_7)-$ group, and $R_6$ is a radical $-CH-R_8-CHR_9-S-CR_{10}R_{11}R_{12}$, wherein each of $R_8$ and $R_9$ independently is a hydrogen atom or a $C_1$-$C_6$-alkyl group, $R_{10}$ is a hydrogen atom, a $C_1$-$C_{19}$-alkyl group, a $C_2$-$C_4$-alkenyl group or an aryl group, $R_{11}$ is a hydrogen atom or a methyl group and $R_{12}$ is a hydrogen atom or a methyl group, or, if $R_{11}$ is a hydrogen atom, is a $C_2$-$C_6$-alkyl group, or, if $R_{10}$ is a hydrogen atom, $R_{11}$ and $R_{12}$ together with the carbon atom to which they are attached represent a cycloalkyl group, or $R_{10}$, $R_{11}$ and $R_{12}$ together with the carbon atom to which they are attached represent an aryl group, or if Y is a thiocarbonyl, sulphinyl or sulphonyl group,
$R_6$ can also be a hydrogen atom or a $C_1$-$C_{18}$-alkyl group or an aryl group, and
$R_7$ is a hydrogen atom, a $C_1$-$C_{18}$-alkyl group or an aryl group, as stabilizers for organic material.

10 Claims, No Drawings

NOVEL PHENOL STABILIZERS

The invention relates to novel phenols which are suitable antioxidants, a process for their manufacture, and to the use thereof for stabilising polymers and organic material which are normally subject to oxidative degradation.

Polycarbonates which are described as effective antioxidants for polyolefins, such as polypropylene, are known from U.S. Pat. No. 3,655,718 and also U.S. Pat. No. 3,510,507, which discloses substantially the same inventive subject matter, and from DT-OS No. 2,016,296. Thus, for example, a polycarbonate of the formula

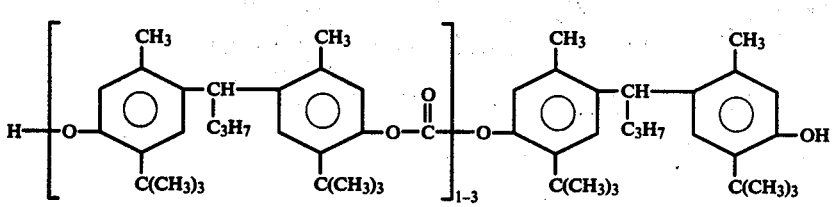

is described as an antioxidant for polyolefins in Example VB of U.S. Pat. No. 3,655,718. Similar compounds are also known from U.S. Pat. No. 3,579,561.

These known polycarbonates are characterised by a methylene group which is positioned between two phenyl radicals and which is unsubstituted or substituted by alkyl or aryl. Although these polycarbonates do have an antioxidative action in polyolefins, this action does not suffice for use in actual practice.

Starting from this prior art, the present invention discloses novel phenols which have an excellent oxidative action when incorporated in polymers, in particular in polyolefins. The novel phenols have the formula I

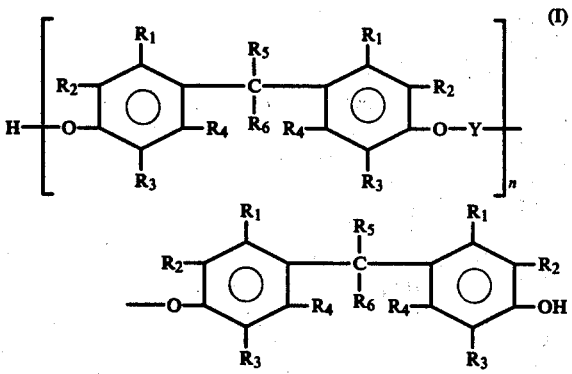

wherein
n has a value from 1 to 15,
each of $R_1$, $R_2$, $R_3$ and $R_4$ independently is a hydrogen atom, a $C_1$-$C_{18}$-alkyl group, an aryl group, a $C_5$-$C_{12}$-cycloalkyl group or a $C_7$-$C_{13}$-aralkyl group,
$R_5$ is a hydrogen atom or a $C_1$-$C_{18}$-alkyl group,
Y is a carbonyl, thiocarbonyl, sulphinyl, sulphonyl, —P(OR$_7$)—, —P(=O)(OR$_7$)—, —P(=O)(R$_7$)— or —P(R$_7$)— group, and
$R_6$ is a radical —CHR$_8$—CHR$_9$—S—CR$_{10}$R$_{11}$R$_{12}$, wherein each of $R_8$ and $R_9$ independently is a hydrogen atom or a $C_1$-$C_6$-alkyl group, $R_{10}$ is a hydrogen atom, a $C_1$-$C_{19}$-alkyl group, a $C_2$-$C_4$-alkenyl group or an aryl group,
$R_{11}$ is a hydrogen atom or a methyl group and
$R_{12}$ is a hydrogen atom or a methyl group, or, if $R_{11}$ is a hydrogen atom, is a $C_2$-$C_6$-alkyl group, or, if $R_{10}$ is a hydrogen atom, $R_{11}$ and $R_{12}$ together with the carbon atom to which they are attached represent a cycloalkyl group, or $R_{10}$, $R_{11}$ and $R_{12}$ together with the carbon atom to which they are attached represent an aryl group, or if Y is a thiocarbonyl, sulphinyl or sulphonyl group,
$R_6$ can also be a hydrogen atom or a $C_1$-$C_{18}$-alkyl group or an aryl group, and
$R_7$ is a hydrogen atom, a $C_1$-$C_{18}$-alkyl group or an aryl group.

A $C_1$-$C_{18}$-alkyl group represented by $R_1$, $R_2$, $R_3$, $R_4$, $R_5$, $R_6$ or $R_7$ can be a straight-chain or branched alkyl group, such as a methyl, ethyl, n-propyl, iso-propyl, n-butyl, sec.-butyl or tert.-butyl group, as well as a branched or straight-chain pentyl, hexyl, n-octyl, tert.-octyl, decyl, dodecyl, tetradecyl, hexadecyl or octadecyl group.

An aryl group represented by $R_1$, $R_2$, $R_3$, $R_4$, $R_6$, $R_7$ or $R_{10}$ is in particular a substituted or unsubstituted phenyl group, such as a phenyl group which is unsubstituted or polysubstituted, or especially monosubstituted, by halogen, such as chlorine, alkyl, such as $C_1$-$C_6$-alkyl, in particular methyl, and/or alkoxy, such as $C_1$-$C_6$-alkoxy, in particular methoxy; preferably, however, an aryl group is an unsubstituted phenyl group.

A $C_1$-$C_6$-alkyl group represented by $R_8$ or $R_9$ is a branched or, in particular, straight-chain alkyl group, such as an ethyl, n-propyl or preferably methyl group.

An alkenyl group represented by $R_{10}$ is in particular an allyl, methallyl or vinyl group.

A cycloalkyl group represented by $R_{11}$ and $R_{12}$ together with the carbon atom to which they are attached is in particular a cyclopentyl or cyclohexyl group. An aryl group represented by $R_{10}$, $R_{11}$ and $R_{12}$ together with the carbon atom to which they are attached is in particular an aryl group as defined above, in particular a phenyl group.

A $C_1$-$C_{19}$-alkyl group represented by $R_{10}$ is a branched, or in particular straight-chain, alkyl group as defined for example for $R_1$, especially a n-butyl, n-octyl, n-dodecyl or n-octadecyl group.

A $C_2$-$C_6$-alkyl group represented by $R_{12}$ is a branched, or in particular straight-chain, alkyl group, such as a n-propyl, n-butyl or especially ethyl group.

Preferred phenols are the phenols Ia of the formula (I) wherein
n is 1 to 4,
$R_1$ is a hydrogen atom or a methyl group,
$R_2$ is a hydrogen atom, a methyl, ethyl or tert.-butyl group,
$R_3$ is a hydrogen atom, a methyl, ethyl or tert.-butyl group, each of
$R_4$ and $R_5$ is a hydrogen atom, Y is a carbonyl, $-P(OR_7)-$, $-P(=O)(OR_7)-$, $-P(=O)(R_7)-$ or $-P(R_7)-$ group, $R_6$ is a radical $-CHR_8-CHR_9-S-CR_{10}R_{11}R_{12}$, $R_8$ is a hydrogen atom, $R_9$ is a hydrogen atom or a methyl group, $R_{10}$ is a $C_4-C_{19}$-n-alkyl group, each of $R_{11}$ and $R_{12}$ is a hydrogen atom, and $R_7$ is a hydrogen atom, a $C_1-C_{18}$-alkyl group or a phenyl group.

Particularly preferred phenols are phenols Ib of the formula (I), wherein n is 1 to 4, $R_1$ is a hydrogen atom or a methyl group, $R_2$ is a hydrogen atom, a methyl, ethyl, or tert.-butyl group, $R_3$ is a hydrogen atom, a methyl, ethyl, or tert.-butyl group, each of $R_4$ and $R_5$ is a hydrogen atom, Y is a carbonyl, $-P(OR_7)-$ or $-P(=O)(OR_7)-$ group, $R_6$ is a radical $-CHR_8-CHR_9-S-CR_{10}R_{11}R_{12}$, $R_8$ is a hydrogen atom, $R_9$ is a hydrogen atom or a methyl group, $R_{10}$ is a $C_4-C_{18}$-n-alkyl or phenyl group, each of $R_{11}$ and $R_{12}$ is a hydrogen atom, and $R_7$ is a $C_1-C_{18}$-n-alkyl or phenyl group.

The most preferred phenols are the phenols Ic of the formula (I) wherein n is 1 or 4, $R_1$ is a methyl group, each of $R_2$, $R_4$ and $R_5$ is a hydrogen atom, $R_3$ is a tert.-butyl group, Y is a carbonyl or $-P(O$-phenyl$)$-group, $R_6$ is a radical $-CH_2-CHR_9-S-CH_2R_{10}$, $R_9$ is a methyl group, and $R_{10}$ is a $C_4-C_{12}$-n-alkyl group, and most preferably the phenols illustrated in the Examples.

In the preferred phenols, Y is likewise sulphinyl or thiocarbonyl.

The novel phenols of the formula (I) can be obtained in a manner known per se, for example by reacting a phenol of the formula (II)

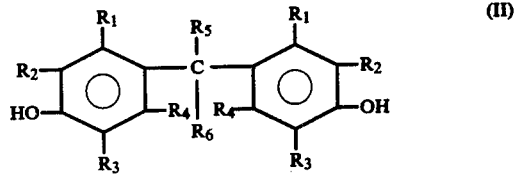

with an acid $Y(OH)_2$ or a reactive derivative thereof, wherein all the symbols are as defined above.

In the above reaction, a reactive derivative of an acid $Y(OH)_2$, such as an acid halide, in particular an acid chloride, or an ester, such as an alkyl or aryl ester, is preferably used. Depending on the definition of Y, examples of suitable acid halides and esters which can be used are: phosgene or a carbonate, such as diphenyl carbonate (Y=carbonyl), thiophosgene (Y=thiocarbonyl), thionyl chloride (Y=thiocarbonyl), thionyl chloride (Y=sulphinyl), sulphuryl chloride (Y=sulphonyl), $R_7O-PCl_2$ or $P(OR_7)_3$ (Y=$-P(OR_7)-$), $R_7O-P(=O)Cl_2$ or $-P(=O)(OR_7)_3$ (Y=$-P(=O)(OR_7)-$), $R_7-P(=O)Cl_2$ or $R_7-P(=O)(OR_7)_2$ (Y=$-P(=O)(R_7)-$), $R_7-PCl_2$ or $R_7-P(OR_7)_2$ (Y=$-P(R_7)-$). For both acid halides and esters it is advantageous to use a catalyst, in particular a basic catalyst. If the starting material is an acid halide, the catalyst is for example an organic nitrogen base, such as pyridine or triethylamine, and if it is an ester, the catalyst is a strong base, such as a metal alcoholate, for example potassium tert.-butylate or lithium amide or the like. It is advantageous to apply heat during the reaction: gentle heating if an acid halide is used and stronger heating if an ester is used, for example the reflux temperature of a solvent employed, such as an aprotic solvent, e.g. an ether, for example tetrahydrofuran or dioxan, or a hydrocarbon, such as toluene or xylene. The basic catalyst can also be used with advantage in equimolar amounts in order to bind the hydrogen halide if the starting material is an acid halide. If an ester is used as starting material, such as a phenyl ester, then the alcohol which forms, for example phenol, can be distilled off, if appropriate until such time as no further distillate passes over. Temperatures of approx. 160° to 250° C. are suitable.

The phenols of the formula (II) are known, for example from U.S. Pat. No. 3,506,716. The acids $Y(OH)_2$ and their reactive derivatives are also known.

According to the present invention, the compounds of the formula I can be used as stabilisers for organic substrates. Suitable substrates are in particular polymers which are derived from hydrocarbons having single or double unsaturation, such as polyolefins, for example polyethylene which may be crosslinked or uncrosslinked, polypropylene, polyisobutylene, polymethylbutene-1, polymethylpentene-1, polybutene-1, polyisoprene, polybutadiene, polystyrene, polyisobutylene, copolymers of the monomers based on the cited homopolymers, such as ethylene-propylene copolymers, propylene-butene-1 copolymers, propylene-isobutylene copolymers, styrene-butadiene copolymers, as well as terpolymers of ethylene and propylene with a diene, for example hexadiene, dicyclopentadiene or ethylenenorbornenes; mixtures of the above mentioned homopolymers, for example mixtures of polypropylene and polyethylene, polypropylene and polybutene-1, polypropylene and polyisobutylene.

Polymers which contain double bonds are also suitable, for example: polymers which are derived from hydrocarbons having double unsaturation, for example polyisopropylene or polybutadiene, polystyrene, copolymers of styrene or α-methylstyrene with dienes or acrylic derivatives, for example styrene-butadiene, styrene-acrylonitrile, styrene-acrylonitrile-methacrylate; mixtures of high impact strength consisting of styrene copolymers and another polymer, for example a polyacrylate, a diene polymer or an ethylene-propylene-diene terpolymer; as well as block copolymers of styrene, for example styrene-butadiene-styrene; styrene-isoprene-styrene or styrene-ethylene/butylene-styrene; graft copolymers of styrene, for example styrene to polybutadiene, styrene and acrylonitrile to polybutadiene, and the mixtures thereof with the copolymers previously mentioned, i.e. those known as ABS polymers.

Oils, such as lubricating oils and hydraulic fluids, are also suitable.

The compounds of the formula I are incorporated in the substrates as a rule in a concentration of 0.01 to 5% by weight, based on the material to be stabilised. Preferably 0.05 to 2%, most preferably 0.1 to 1% by weight of the compounds, based on the material to be stabilised, are incorporated thereinto. The incorporation can be accomplished for example by blending in at least one of the compounds of the formula I and optionally further additives by methods which are commonly employed in the art, before or during the forming, or also by applying solutions or dispersions of the compounds to the polymers, if appropriate after subsequent evaporation of the solvent.

If the substrate is crosslinked polyethylene, the compounds of the formula I are advantageously added before the crosslinking. The compounds of the formula I can also be added before or during the polymerisation.

Examples of further additives together with which the stabilisers can be used are: antioxidants, UV absorbers, light stabilisers, phosphites, compounds which decompose peroxide, basic costabilisers, nucleating agents and other customary additives.

The following Examples illustrate the invention in more detail. Parts and percentages are by weight.

EXAMPLE 1

While scavenging with nitrogen, 1.7 ml (0.0034 mole) of a 20% solution of phosgene in toluene are added dropwise over the course of 20 minutes to a mixture of 4.5 parts (0.0067 mole) of 1,1-bis-(3-tert.-butyl-4-hydroxy-6-methyl-phenyl)-3-methyl-3-n-octadecylthiopropane. During the addition, the temperature rises from 20° to 29° C. The reaction mixture is stirred for 2 hours at room temperature and the pyridine hydrochloride is subsequently removed by filtration. The filtrate is washed neutral with water, the toluene phase is dried over sodium sulphate and the toluene is stripped off in vacuo to give the desired carbonate as an amorphous residue with a molecular weight of 988.

EXAMPLE 2

The procedure of Example 1 is repeated using 32.5 parts (0.057 mole) of 1,1-bis-(3-tert.-butyl-4-hydroxy-6-methylphenyl)-3-n-dodecylthiopropane, 80 ml of ether, 7.4 ml of pyridine and 4.5 parts (0.046 mole) of phosgene, to give the desired carbonate as an amorphous residue with a molecular weight of 1210.

EXAMPLE 3

The procedure of Example 1 is repeated using 12.5 parts (0.025 mole) of 1,1-bis-(3-tert.-butyl-4-hydroxy-6-methylphenyl)-3-p-butylthiobutane, 40 ml of abs. ether, 3.7 ml of pyridine and 2.3 parts (0.023 mole) of phosgene, to give the desired carbonate as a white powder with a molecular weight of 877, which is the compound claimed in claim 7.

EXAMPLE 4

13.15 parts (0.025 mole) of 1,1-bis-(3-tert.-butyl-4-hydroxy-6-methyl-phenyl)-3-methyl-4-thiadodecane, 5.35 parts (0.025 mole) of diphenyl carbonate and 0.1 part of freshly sublimed potassium tert.-butoxide are placed in an apparatus set up for distillation. The ingredients are heated together at 120° C. under vacuum (approx. 27 mm Hg) to form a melt, and then the temperature is raised slowly to 210° C. During this time, 3.1 parts distill into the receiver flask. The reaction is complete after approx. 1 hour. After cooling, the solid polycarbonate is dissolved in chloroform. The solvent is evaporated off to give 12.3 parts of a finely crystalline product with a molecular weight of 2305.

EXAMPLE 5

15.8 parts (0.03 mole) of 1,1-bis-(3-tert.-butyl-4-hydroxy-6-methyl-phenyl)-3-methyl-4-thiodecane and 3.8 parts (0.048 mole) of dry pyridine are placed in a reaction flask equipped with a mechanical stirrer, thermometer, condenser and inlet tube. After the addition of 100 parts of anhydrous ether, phosgene is passed slowly into the resultant solution at 35°-40° C. until 2.4 parts (0.024 mole) are absorbed. The reaction mixture is stirred at room temperature for 16 hours under an atmosphere of nitrogen. The pyridine hydrochloride is removed by filtration and the ether evaporated to give 14.1 parts of a crude product. This crude product is recrystallised from water-methanol (1:1) and dried in the oven at 70° C., affording 10.6 parts of a white crystalline product with a molecular weight of 737.

EXAMPLE 6

To a solution of 26.3 parts (0.05 mole) of 1,1-bis-(3-tert.-butyl-4-hydroxy-6-methyl-phenyl)-3-methyl-4-thiodecane, 6.3 parts (0.08 mole) of water-free pyridine in 100 parts by volume of dry ether are added dropwise 3 parts by volume (0.04 mole) of thionyl chloride. The reaction is exothermic. The reaction mixture is stirred under slight reflux for 4 hours and then left for 16 hours at 23° C. The pyridine hydrochloride is filtered off and the organic phase washed several times with water. Drying over sodium sulphate and removal of the ether gives a yellow oil which crystallises on standing at room temperature. Recrystallisation from methanol gives 18.5 parts of a white amorphous-like product which is the polysulphite (molecular weight: 1845).

EXAMPLE 7

3 parts by volume (0.04 mole) of thionyl chloride are added dropwise to a solution of 19.1 parts (0.05 mole) of 1,1-bis-(3-tert.-butyl-4-hydroxy-6-methyl-phenyl)-n-butane and 6.3 parts (0.08 mole) of pyridine in 100 parts by volume of dry ether. The reaction mixture is refluxed under nitrogen for 4 hours, then cooled, and the pyridine hydrochloride carefully removed by filtration. Working up in the usual way gives a viscous oil which solidifies on being left overnight at room temperature. Recrystallisation from methanol gives 9.4 parts of a white crystalline product which is the polysulphite (molecular weight: 1845).

EXAMPLE 8

13.15 parts (0.025 mole) of 1,1-bis-(3-tert.-butyl-4-hydroxy-6-methyl-phenyl)-3-methyl-4-thiododecane and 3.2 parts (0.04 mole) of pyridine dissolved in 100 parts by volume of dry ether are treated dropwise with 1.6 parts by volume (0.02 mole) of thiophosgene. The reaction mixture is gently refluxed for 4 hours, cooled, and the pyridine hydrochloride is filtered off. After washing with water, the organic phase is dried and the ether evaporated to give a green coloured polythiocarbonate which is recrystallised from methanol. Yield: 11.1 parts (molecular weight: 755).

EXAMPLE 9

To 9.55 parts (0.025 mole) of 1,1-bis-(3-tert.-butyl-4-hydroxy-6-methyl-phenyl)-butane and 3.15 parts (0.04 mole) of pyridine dissolved in 100 parts by volume of ether are added dropwise 1.6 parts by volume (0.2 mole) of thiophosgene. The reaction mixture is heated to 36° C. for 4 hours, cooled, and worked up as described in Example 5 to give 8.2 parts of a polycarbonate with a molecular weight of 427.

EXAMPLE 10

13.15 parts (0.025 mole) of 1,1-bis-(3-tert.-butyl-4-hydroxy-6-methyl-phenyl)-3-methyl-4-thiadodence and 7.8 parts (0.025 mole) of triphenyl-phosphite together with approx. 0.1 part (approx. 0.01 mole) of freshly sublimed potassium tert.-butoxide are heated under vacuum (1 mm Hg) to 180° C. over a period of 2 hours. The reaction mixture melts at approx. 90° C., is then allowed to cool, and the product is dissolved in chloroform. The solvent is evaporated off to give 10.2 parts of a crude product which is recrystallised from methanol and dried in the oven at 40° C. to yield 8 parts of a white crystalline polyphosphite.

EXAMPLE 11

11.6 parts (0.02 mole) of 1,1-bis-(3-tert.-butyl-4-hydroxy-6-methyl-phenyl)-3-methyl-4-thiahexadecane, 6.1 parts (0.02 mole) of triphenylphosphite and 0.1 part of potassium tert.-butoxide are fused together at 180° C. (18 mm Hg) for 2½ hours. The working up is the same as described in Example 10, giving 10 parts of a white crystalline polyphosphite.

EXAMPLE 12

A mixture of 13.9 parts (0.025 mole) of 1,1-bis-(3-tert.-butyl-4-hydroxy-6-methyl-phenyl)-3-methyl-4-thiatetradecane, 7.8 parts (0.025 mole) of triphenylphosphite, containing a catalytic amount of potassium tert.-butoxide (0.1 mole), is heated for 2½ hours at 90° C. Working up as described in Examples 10 and 11 give 11 parts of a low melting polyphosphite with a molecular weight of 860.

EXAMPLE 13

A mixture of 23.5 parts (0.05 mole) of 1,1-bis-(3-tert.-butyl-4-hydroxy-6-methyl-phenyl)-3-methyl-4-thiaoctane and 15.5 parts (0.05 mole) of triphenylphosphite, containing 0.2 part of potassium tert.-butoxide, are fused together at 180° C. for 4 hours. Working up as described in Examples 10, 11 and 12 give 17 parts of a crystalline polyphosphite.

EXAMPLE 14

13.17 parts (0.025 mole) of 1,1-bis-(3-tert.-butyl-4-hydroxy-6-methyl-phenyl)-3-methyl-4-thiadodecane and 8.15 parts (0.025 mole) of triphenylphosphate, in the presence of 0.1 part of potassium tert.-butoxide, are heated together at 180° C. for 2 hours. The solid mass is well washed with chloroform and dried, giving 11.1 parts of a slightly discoloured polyphosphate.

EXAMPLE 15

13.5 parts (0.025 mole) of 1,1-bis-(3-tert.-butyl-4-hydroxy-6-methyl-phenyl)-3-methyl-4-thiatetradecane, 8.15 parts of triphenylphosphite and 0.1 part of potassium tert.-butoxide are fused together at 90° C. (16 mm Hg) for 1½ hours. The temperature is raised slowly to 130° C. and the melt is stirred at this temperature for 2 hours. Recrystallisation of the product from chloroform gives 11.3 parts of polyphosphate as a white crystalline solid with a molecular weight of 2.345.

EXAMPLE 16

10.5 parts (0.02 mole) of 1,1-bis-(3-tert.-butyl-4-hydroxy-6-methyl-phenyl)-3-methyl-4-thiadodecane, 3.2 parts (0.01 mole) of triphenylphosphate and 0.1 part of potassium tert.-butoxide are heated together for 2½ hours at 175° C. Working up as described in Example 14 gives 7.2 parts of a polyphosphate as a powder-like substance.

EXAMPLE 17

Fusion of 13.9 parts of 1,1-bis-(3-tert.-butyl-4-hydroxy-6-methyl-phenyl)-3-methyl-4-thiatetradecane, 5.35 parts of diphenyl carbonate and 0.1 part of potassium tert.-butoxide under vacuum (20 mm Hg) for 4½ hours and working up as described in Example 4 give 11.9 parts of a polycarbonate as a white crystalline solid with a molecular weight of 665.

EXAMPLE 18

1.43 parts by volume (0.02 mole) of thionyl chloride are added dropwise at 24° C. to a solution of 13.9 parts (0.025 mole) of 1,1-bis-(3-tert.-butyl-4-hydroxy-6-methyl-phenyl)-3-methyl-4-thiatetradecane in 150 parts by volume of ether containing 3.2 parts by volume (0.04 mole) of pyridine. The reaction mixture is then refluxed for 4 hours and worked up as described in Examples 6 and 7 to give 9.1 parts of a white crystalline polysulphite with a molecular weight of 932.

EXAMPLE 19

100 parts of polypropylene (melt index 3.2 g/10 mins., 230° C./2160 g) are thoroughly mixed for 10 minutes in a shaking apparatus with 0.2 part of one of the additives listed in the following Table.

The resulting mixture is kneaded for 10 minutes at 200° C. in a Brabender plastograph and the composition thus obtained is subsequently pressed to 1 mm thick sheets in a day-light press at a temperature of 260° C. Strips 1 cm wide and 17 cm long are punched from these sheets.

The test of the effectiveness of the additive incorporated in the test strips is carried out by means of oven ageing in a forced draught oven at 135° C. and 149° C., a test strip which contains no additive serving as comparison. Three test strips of each formulation are used for this purpose. The end point is defined as the onset of the slightly visible decomposition of the test strip.

Table

| Stabiliser | No. of days until beginning of decomp. | |
|---|---|---|
| Example | 149° | 135° |
| None | 1 | 3 |
| (1) | 29 | 76 |
| (2) | 9 | 47 |
| (3) | 43 | 85 |
| (4) | 26 | 54 |
| (5) | 29 | 66 |
| (6) | 24 | 54 |
| (7) | 23 | 73 |
| (10) | 25 | 55 |
| (11) | 19 | 57 |
| (17) | 27 | 64 |
| (18) | 25 | 54 |
| Comparison* | 1 | 9 |

*Product of Example VB, U.S. Pat. specification 3,655,718.

I claim:

1. A phenol of the formula I

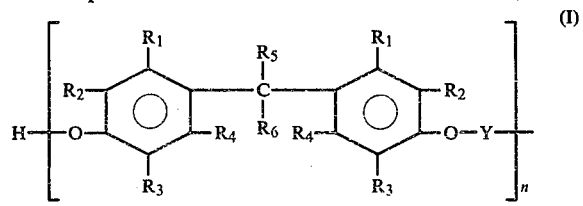

-continued

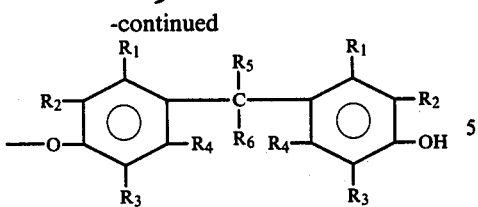

wherein
n has a value from 1 to 15,
each of $R_1$, $R_2$, $R_3$ and $R_4$ independently is a hydrogen atom, a $C_1$-$C_{18}$-alkyl group, an aryl group, a $C_5$-$C_{12}$-cycloalkyl group or a $C_7$-$C_{13}$-aralkyl group,
$R_5$ is a hydrogen atom or a $C_1$-$C_{18}$-alkyl group,
Y is carbonyl, and
$R_6$ is a radical —$CHR_8$—$CHR_9$—S—$CR_{10}R_{11}R_{12}$, wherein each of $R_8$ and $R_9$ independently is a hydrogen atom or a $C_1$-$C_6$-alkyl group, $R_{10}$ is a hydrogen atom, a $C_1$-$C_{19}$-alkyl group, a $C_2$-$C_4$-alkenyl group or an aryl group, $R_{11}$ is a hydrogen atom or a methyl group and $R_{12}$ is a hydrogen atom or a methyl group, or, $R_{11}$ is a hydrogen atom and $R_{12}$ is a $C_2$-$C_6$-alkyl group, or, $R_{10}$ is a hydrogen atom and $R_{11}$ and $R_{12}$ together with the carbon atom to which they are attached represent a cycloalkyl group, or $R_{10}$, $R_{11}$ and $R_{12}$ together with the carbon atom to which they are attached represent an aryl group.

2. A phenol according to claim 1, wherein
n is 1 to 4,
$R_1$ is a hydrogen atom or a methyl group,
$R_2$ is a hydrogen atom, a methyl, ethyl or tert.-butyl group,
$R_3$ is a hydrogen atom, a methyl, ethyl or tert.-butyl group,
each of $R_4$ and $R_5$ is a hydrogen atom,
Y is carbonyl,
$R_6$ is a radical —$CHR_8$—$CHR_9$—S—$CR_{10}R_{11}R_{12}$,
$R_8$ is a hydrogen atom,
$R_9$ is a hydrogen atom or a methyl group,
$R_{10}$ is a $C_4$-$C_{19}$-n-alkyl group, and each of $R_{11}$ and $R_{12}$ is a hydrogen atom.

3. A phenol according to claim 1, wherein
n is 1 to 4,
$R_1$ is a hydrogen atom or a methyl group,
$R_2$ is a hydrogen atom, a methyl, ethyl, or tert.-butyl group,
$R_3$ is a hydrogen atom, a methyl, ethyl, or tert.-butyl group,
each of $R_4$ and $R_5$ is a hydrogen atom,
Y is carbonyl,
$R_6$ is a radical —$CHR_8$—$CHR_9$—S—$CR_{10}R_{11}R_{12}$,
$R_8$ is a hydrogen atom,
$R_9$ is a hydrogen atom or a methyl group,
$R_{10}$ is a $C_4$-$C_{18}$-n-alkyl or phenyl group, each of $R_{11}$ and $R_{12}$ is a hydrogen atom.

4. A phenol according to claim 1, wherein
n is 1 or 4,
$R_1$ is a methyl group,
each of $R_2$, $R_4$ and $R_5$ is a hydrogen atom,
$R_3$ is a tert.-butyl group,
Y is carbonyl,
$R_6$ is a radical —$CH_2$-$CHR_9$—S—$CH_2R_{10}$,
$R_9$ is a methyl group, and
$R_{10}$ is a $C_4$-$C_{12}$-n-alkyl group.

5. A phenol according to claim 1, wherein
$R_1$ is a methyl group,
each of $R_2$, $R_4$ and $R_5$ is a hydrogen atom,
$R_3$ is a tert.-butyl group, and
Y is a carbonyl group.

6. An organic material which contains a compound according to claim 1 in an amount sufficient to stabilize the organic material against oxidation.

7. A stabilized organic material according to claim 6 wherein the organic material is an organic polymer.

8. A stabilized organic material according to claim 7 wherein the organic polymer is a polyolefin.

9. A stabilized organic material according to claim 8, wherein the polyolefin is polypropylene.

10. A process for stabilizing organic material against oxidation which comprises incorporating thereinto a compound according to claim 1.

* * * * *